United States Patent
Allard

(10) Patent No.: US 11,944,847 B2
(45) Date of Patent: Apr. 2, 2024

(54) SYSTEM AND METHOD FOR OPEN-LOOP ULTRASOUND THERAPY TO THE PROSTATE INCLUDING RESTRICTING THE THERAPY DELIVERED TO A PREDETERMINED ANGULAR RANGE

(71) Applicant: Profound Medical Inc., Mississauga (CA)

(72) Inventor: Mathieu Allard, Mississauga (CA)

(73) Assignee: Profound Medical Inc., Mississauga (CA)

(*) Notice: Subject to any disclaimer, the term of this patent is extended or adjusted under 35 U.S.C. 154(b) by 288 days.

(21) Appl. No.: 16/984,367

(22) Filed: Aug. 4, 2020

(65) Prior Publication Data
US 2021/0038923 A1 Feb. 11, 2021

Related U.S. Application Data

(60) Provisional application No. 62/882,662, filed on Aug. 5, 2019.

(51) Int. Cl.
*A61N 7/00* (2006.01)

(52) U.S. Cl.
CPC ........ *A61N 7/00* (2013.01); *A61N 2007/0004* (2013.01); *A61N 2007/0043* (2013.01);
(Continued)

(58) Field of Classification Search
CPC .............. A61N 7/00; A61N 2007/0004; A61N 2007/0043; A61N 2007/0052;
(Continued)

(56) References Cited

U.S. PATENT DOCUMENTS 5,759,162 A * 6/1998 Oppelt ..................... A61N 7/02
 601/2
8,801,615 B2 * 8/2014 Fernandez ............. A61N 7/022
 600/439

(Continued)

FOREIGN PATENT DOCUMENTS

| EP | 2334375 B1 | 8/2013 |
| WO | 9316641 A1 | 9/1993 |
| WO | 2018183217 A1 | 10/2018 |

OTHER PUBLICATIONS

ISA, "International Search Report", PCT/CA2020/051066, dated Nov. 5, 2020.
(Continued)

*Primary Examiner* — Serkan Akar
*Assistant Examiner* — Gabriel Victor Popescu
(74) *Attorney, Agent, or Firm* — Intrinsic Law Corp.

(57) ABSTRACT

A method for delivering ultrasound therapy using open-loop controls comprises inserting a distal tip of a therapeutic ultrasound applicator into a patient's urethra, the distal tip including an ultrasound transducer; acquiring ultrasound images of the patient's urethra and prostate with an ultrasound imaging probe; aligning the distal tip of the therapeutic ultrasound applicator with the patient's prostate using the ultrasound images; delivering therapeutic ultrasound energy to the patient's prostate, with the ultrasound transducer, according to a treatment plan, the treatment plan including a predetermined limited angular range for the therapeutic ultrasound energy that avoids the patient's rectum and neurovascular bundles, wherein the therapeutic ultrasound is delivered without temperature feedback data.

12 Claims, 4 Drawing Sheets

(52) U.S. Cl.
CPC ............. *A61N 2007/0052* (2013.01); *A61N 2007/0078* (2013.01); *A61N 2007/0086* (2013.01)

(58) Field of Classification Search
CPC .... A61N 2007/0078; A61N 2007/0086; A61N 7/022; A61N 2007/0091; A61B 2090/378; A61B 34/10; A61B 2034/107
See application file for complete search history.

(56) References Cited

U.S. PATENT DOCUMENTS

| | | | |
|---|---|---|---|
| 10,286,228 B2 | 5/2019 | Bharat et al. | |
| 2003/0060856 A1* | 3/2003 | Chornenky | A61B 18/12 607/40 |
| 2005/0070961 A1* | 3/2005 | Maki | A61N 7/022 607/2 |
| 2010/0241005 A1* | 9/2010 | Darlington | A61N 7/02 600/437 |
| 2011/0295161 A1* | 12/2011 | Chopra | A61N 7/022 607/40 |
| 2012/0215106 A1* | 8/2012 | Sverdlik | A61N 7/00 600/439 |
| 2014/0058294 A1* | 2/2014 | Gross | A61N 7/022 601/2 |
| 2014/0330124 A1* | 11/2014 | Carol | A61N 7/022 600/439 |
| 2017/0304656 A1 | 10/2017 | Kurtz et al. | |
| 2018/0280089 A1* | 10/2018 | Elevelt | A61B 2034/107 |
| 2019/0209119 A1* | 7/2019 | Mauldin, Jr. | A61B 8/5223 |

OTHER PUBLICATIONS

European Patent Office, extended European Search Report for EP Application No. 20849571.3 dated Jul. 14, 2023.

* cited by examiner

SYSTEM AND METHOD FOR OPEN-LOOP ULTRASOUND THERAPY TO THE PROSTATE INCLUDING RESTRICTING THE THERAPY DELIVERED TO A PREDETERMINED ANGULAR RANGE

CROSS-REFERENCE TO RELATED APPLICATIONS

This application claims priority to U.S. Provisional Application No. 62/882,662, filed Aug. 5, 2019, titled "Open-Loop Ultrasound Therapy," which is hereby incorporated by reference.

TECHNICAL FIELD

This application relates generally to ultrasound therapy for medical conditions.

BACKGROUND

Existing ultrasound treatment systems such as focused ultrasound therapy and surgery systems require or benefit from guidance, which can be provided by ultrasound, magnetic resonance imaging (MRI) or other methods. Guidance can assist the operator (human or machine) to spatially and/or temporally control the application of focused ultrasound to direct therapeutic thermal energy onto a desired (e.g., diseased) target or region of interest.

MRI guidance is an expensive proposition, which requires placing a patient and MRI-compatible therapy equipment in special environments so as to monitor the therapy using MR thermometry methods. Specialized MRI radiologists are required to operate and monitor MRI-guided thermal therapy facilities and procedures. In addition, since MRI guidance requires immobilizing the patient (to avoid movement artefacts and interference) MR-guided procedures can require general anesthesia of the patient, which is another complicated and expensive undertaking. Such operations are not portable and are not accessible to sites that lack MRI facilities.

Certain procedures may be achieved without the need for high-precision real-time imaging such as MRI imaging, and less costly and more accessible solutions in thermal therapy such as ultrasound heat therapy are desirable.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a method for delivering ultrasound therapy using open-loop controls. The method includes inserting a distal tip of a therapeutic ultrasound applicator into a patient's urethra, the distal tip including an ultrasound transducer; acquiring ultrasound images of the patient's urethra and prostate with an ultrasound imaging probe; aligning the distal tip of the therapeutic ultrasound applicator with the patient's prostate using the ultrasound images; delivering therapeutic ultrasound energy to the patient's prostate, with the ultrasound transducer, according to a treatment plan, the treatment plan including a predetermined limited angular range for the therapeutic ultrasound energy that avoids the patient's rectum, neurovascular bundles, and internal organs other than the patient's prostate. The therapeutic ultrasound is delivered without temperature feedback data.

In one or more embodiments, the method further comprises registering the ultrasound images with a reference location on the therapeutic ultrasound applicator to provide registered ultrasound images. In one or more embodiments, the reference location comprises a fiducial mark. In one or more embodiments, the method further comprises, in a computer, defining the treatment plan using the registered ultrasound images. In one or more embodiments, defining the treatment plan includes setting a predetermined limited radial range for the therapeutic ultrasound energy that avoids a region immediately beyond the patient's prostate. In one or more embodiments, defining the treatment plan includes setting a predetermined limited axial range for the therapeutic ultrasound energy between a base and an apex of the patient's prostate.

In one or more embodiments, the predetermined limited angular range corresponds to an anterior direction in the patient. In one or more embodiments, the predetermined limited angular range is 0° to 280°. In one or more embodiments, the predetermined limited angular range is 0° to 240°, and 240° corresponds to the prostate's transition region.

In one or more embodiments, the method further comprises mechanically coupling the therapeutic ultrasound applicator to an ultrasound applicator positioning system. In one or more embodiments, the method further comprises automatically aligning the distal tip of the therapeutic ultrasound applicator with the patient's prostate using the ultrasound applicator positioning system. In one or more embodiments, the method further comprises rotating the therapeutic ultrasound applicator, with the ultrasound applicator positioning system, over the predetermined limited angular range while the therapeutic ultrasound energy is delivered.

In one or more embodiments, the method further comprises displaying the ultrasound images on a display that is in electrical communication with the ultrasound imaging probe. In one or more embodiments, the distal tip of the therapeutic ultrasound applicator includes a plurality of ultrasound transducers that are disposed about at least a portion of a circumference of the distal tip, and the method further comprises simultaneously delivering therapeutic ultrasound energy to the patient's prostate, with the ultrasound transducers, in multiple angular directions. In one or more embodiments, the method further comprises rotating the therapeutic ultrasound applicator so that the ultrasound transducers, in combination, are swept across the predetermined limited angular range while simultaneously delivering therapeutic ultrasound energy to the patient's prostate in multiple angular directions.

In one or more embodiments, the therapeutic ultrasound is delivered without MRI thermometry feedback data. In one or more embodiments, the ultrasound imaging probe is integrated into the therapeutic ultrasound applicator.

Another aspect of the invention is directed to a system for open-loop ultrasound therapy delivery. The system comprises a therapeutic ultrasound applicator having a distal tip that includes an ultrasound transducer; an ultrasound imaging probe that acquires ultrasound images of the patient's urethra and prostate; an ultrasound applicator positioning system mechanically coupled to the therapeutic ultrasound applicator; a microprocessor-based UA positioning system controller in electrical communication with the ultrasound applicator positioning system, the UA positioning system controller configured to adjust a position and orientation of the ultrasound transducer to deliver therapeutic ultrasound energy to the patient's prostate according to a treatment plan; and a microprocessor-based computer in electrical communication with the therapeutic ultrasound applicator, the ultrasound imaging probe, and the UA positioning system controller, the computer having a non-volatile memory that stores computer-readable instructions that, when executed by the microprocessor, cause the computer to: receive one or more inputs corresponding to the treatment plan, the treatment plan including a predetermined limited angular range for the therapeutic ultrasound energy that avoids the patient's rectum, neurovascular bundles, and internal organs other than the patient's prostate, and generate control signals that cause the UA positioning system controller to rotate the ultrasound transducer over the predetermined limited angular range and to simultaneously deliver therapeutic ultrasound energy from the ultrasound transducer over the predetermined limited angular range. The therapeutic ultrasound is delivered without temperature feedback data.

In one or more embodiments, the computer-readable instructions further cause the computer to automatically register the ultrasound images with a reference location on the therapeutic ultrasound applicator. In one or more embodiments, the reference location includes a fiducial mark.

In one or more embodiments, the treatment plan includes a predetermined limited radial range for the therapeutic ultrasound energy that avoids a region immediately beyond the patient's prostate. In one or more embodiments, the treatment plan includes a predetermined limited axial range for the therapeutic ultrasound energy between a base and an apex of the patient's prostate. In one or more embodiments, the predetermined limited angular range corresponds to an anterior direction in the patient. In one or more embodiments, the predetermined limited angular range is 0° to 280°. In one or more embodiments, the predetermined limited angular range is 0° to 240°, and 0° and 240° correspond to the prostate's transition regions.

In one or more embodiments, the computer-readable instructions further cause the computer to send a display output signal to a computer display to display the ultrasound images. In one or more embodiments, the UA positioning system controller is further configured to automatically align the distal tip of the therapeutic ultrasound applicator with the prostate using the ultrasound images. In one or more embodiments, the ultrasound imaging probe is integrated into the therapeutic ultrasound applicator. In one or more embodiments, the computer-readable instructions further cause the computer to determine a position of the therapeutic ultrasound applicator relative to the patient's prostate.

BRIEF DESCRIPTION OF THE DRAWINGS

For a fuller understanding of the nature and advantages of the present concepts, reference is made to the detailed description of preferred embodiments and the accompanying drawings.

DETAILED DESCRIPTION

Figure 1:
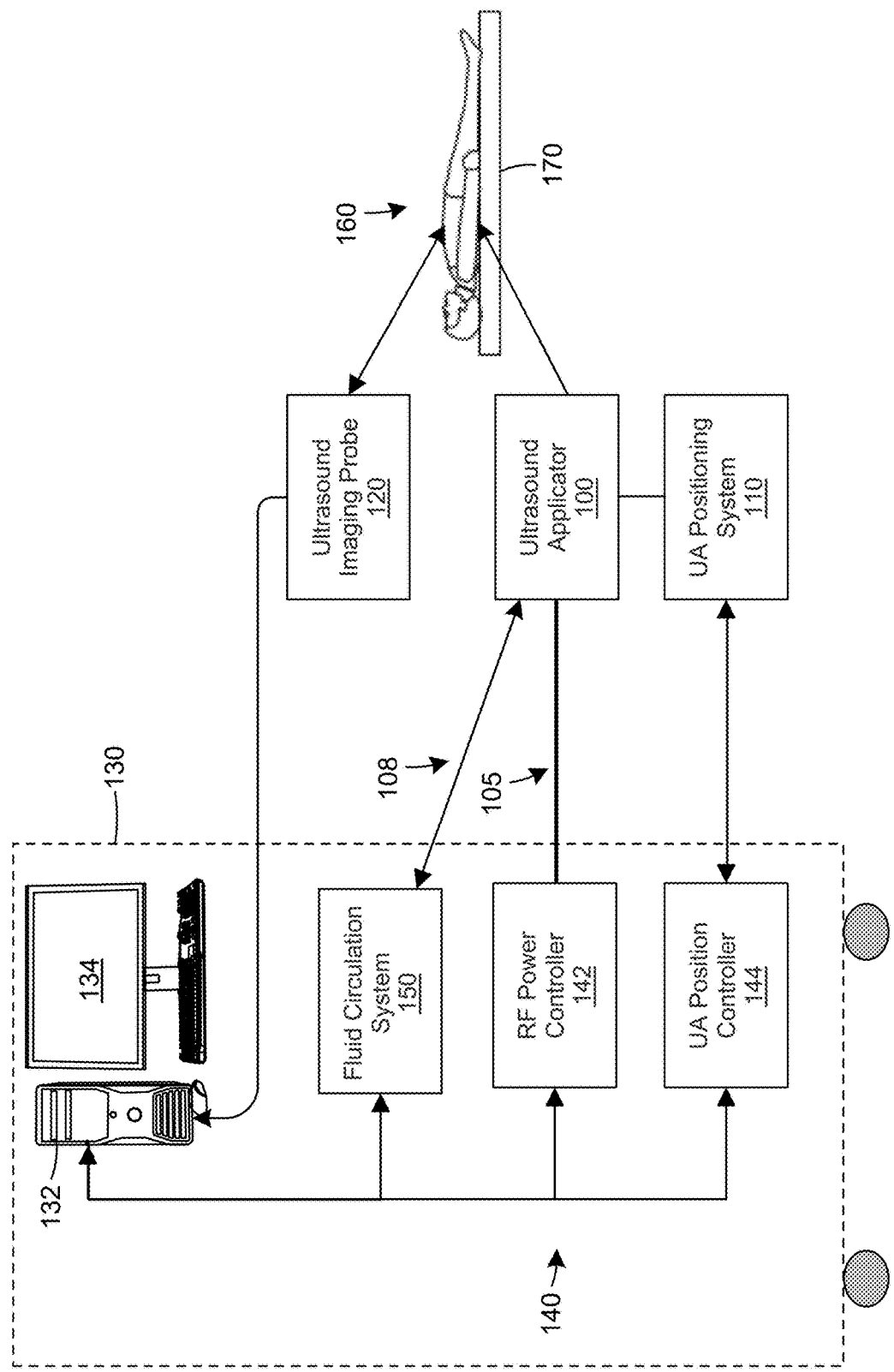
FIG. 1 is a block diagram of an open-loop ultrasound treatment system according to one or more embodiments.

An open-loop ultrasound treatment system is used to deliver ultrasound energy to a target volume without MRI feedback information that is typically available in existing closed-loop ultrasound treatment systems. Specifically, in connection with ultrasound thermal therapy of diseased tissue volumes, e.g., diseased prostates, the present system and method can be used to adequately provide conformal ultrasound therapy from an ultrasound applicator inserted into a patient's body. One application is the treatment of benign prostatic hyperplasia (BPH, also known as prostate enlargement), but other applications and target tissues are possible. Here, an elongated ultrasound applicator may be inserted into a patient's urethra and positioned approximately at a suitable location to deliver therapeutic ultrasound energy at or within the diseased volume. The ultrasound applicator includes a plurality of elements, each providing a directional ultrasound beam, with the direction of the beam adjustable by rotating the applicator. Additionally, cooling of non-diseased (especially critical or sensitive) tissues near the target volume can also be achieved in some aspects. For example, a rectal cooling device designed and operated to remove heat from the rectal wall and its vicinity may be operated in conjunction with the above treatment. In yet other aspects, ultrasound imaging of the regions at or near the treatment location can be used in one or more embodiments.

The open-loop ultrasound treatment system includes an ultrasound applicator that is inserted transurethrally into the patient's prostate. The position of the ultrasound applicator can then be finely tuned, using an ultrasound applicator positioning system that can be computer-controlled, to align the ultrasound transducer(s) on the insertion end of the ultrasound applicator with the prostate. For example, an ultrasound imaging probe, such as a transrectal ultrasound probe and/or a transvesicle ultrasound probe, can generate ultrasound image data of the prostate and urethra, and the user can use the ultrasound image data (e.g., depicted on a computer display) to direct or inform the user or the system as to how and where to apply and position the ultrasound transducer(s) on the insertion end of the ultrasound applicator to align the same with the prostate. In one embodiment, the ultrasound applicator includes ultrasound fiducial markers so that the position of the ultrasound applicator can be unambiguously inferred from the ultrasound images obtained from the ultrasound probe. In another embodiment, the ultrasound probe elements are integrated directly into the ultrasound applicator and are used to image the tissues surrounding the ultrasound applicator to determine its position with respect to the prostate.

In addition, the user can use the ultrasound image data, shown on a computer screen, to create a treatment plan for ablating the prostate. The treatment plan can include parameters that define a treatment volume in the prostate. The parameters can include an axial component, a radial component, and an angular-range component. The radial and angular-range components are defined in a plane that is orthogonal to the axis of the axial component. Alternatively, the treatment plan can be an arbitrary volume surrounding the urethra. The treatment plan is created so that the ultrasound applicator directs ultrasound energy generally in the anterior direction, away from the rectum, nerve bundles, and internal organs other than the rectum, to increase patient safety.

The computer controls the ultrasound applicator according to the treatment plan to insonify and ablate the treatment volume in the prostate. Control is achieved by modulating the acoustic power and the ultrasound frequency emitted by each ultrasound element on the applicator, and by continuously rotating the ultrasound applicator at an adjustable speed. Other parameters may be also controlled such as a driving frequency of the ultrasound transducers. During treatment, the computer can display ultrasound images (e.g., sagittal) collected by the ultrasound imaging probe, which can be integrated into the ultrasound applicator. The computer can also display a progress indicator showing the percentage of the treatment volume that has been insonified.

FIG. 1 is a block diagram of an open-loop ultrasound treatment system 10 according to one or more embodiments. The system 10 includes an ultrasound applicator (UA) 100, a UA positioning system 110, an ultrasound imaging probe 120, and a system cart 130. The system cart 130 includes a computer 132, a computer display 134, systems electronics 140, and a fluid circulation system 150. The system cart 130 can include wheels or casters to facilitate portability.

An example of the UA 100 is described in U.S. Pat. No. 9,707,413, titled "Controllable Rotating Ultrasound Therapy Applicator," issued on Jul. 18, 2017, which is hereby incorporated by reference. An example of the UA positioning system 110 is disclosed in U.S. patent application Ser. No. 16/248,246, titled "Therapeutic Applicator Positioning System With Passive and Active Positioning," filed on Jan. 15, 2019, which is hereby incorporated by reference.

The computer 132 includes a hardware-based microprocessor, memory that is operatively coupled to the microprocessor, network ports, I/O ports, a graphics processor, and other components. The memory includes non-volatile memory that stores computer-readable instructions (e.g., software) that can be executed by the microprocessor to perform one or more operations, functions, and/or tasks.

The systems electronics 140 include an RF power controller 142 that generates driving signals for powering the UA 100 at a desired frequency and amplitude (power). The driving signals are sent to the UA 100 via one or more RF cables 105. An example of the RF power control unit is disclosed in U.S. Pat. No. 9,931,523, titled "RF Power Controller for Ultrasound Therapy System," issued on Apr. 3, 2018, which is hereby incorporated by reference. The UA 100 can be used to perform ultrasound therapy on a target volume in a patient 160, who may be in a supine position on a patient support 170. In one example, the target volume corresponds to a tumor and the ultrasound therapy includes generating sufficient energy, using ultrasound energy, to ablate the tumor.

The systems electronics 140 also include a UA positioning system controller 144 that generates optional motion control signals for the UA positioning system 110 to align the UA 100 with the prostate. The motion control signals can be based, at least in part, on image data outputted from the ultrasound imaging probe 120. The ultrasound imaging probe 120 can be a transrectal ultrasound (TRUS) probe, a transvesicle ultrasound probe, a probe integrated into the UA, or another ultrasound imaging probe. Data representing ultrasound images is sent from the ultrasound imaging probe 120 to the computer 132 which can optionally render and display the ultrasound images on display 134.

The fluid circulation system 150 recirculates cooling fluid (e.g., water) to the UA 100. The fluid circulation system 150 includes a fluid circulation pump and a cooling unit (e.g., a chiller, heat exchanger, etc.) to circulate the cooling fluid between (a) the UA 100 to cool the UA 100 during operation and (b) the cooling unit where the heated cooling fluid is cooled to a predetermined temperature set point, such as room temperature or another temperature. The fluid circulation pump can be a peristaltic pump or another pump A tube set 108 can fluidly couple the UA 100 and the fluid circulation system 150. In some embodiments, the fluid circulation system 150 includes a degasser that removes air bubbles from the cooling fluid.

The computer 132 is in electrical communication (e.g., via wired and/or wireless connections) with the system electronics 140 and the fluid circulation system 150. Through the electrical connection, the computer 132 can send control signals to any of the system electronics 140 or the fluid circulation system 150 and can receive data or other information from any of the system electronics 140 or the fluid circulation system 150. For example, the computer 132 can send RF power control signals to the RF controller 142 that cause the RF controller 142 to generate driving signals having a frequency and amplitude for powering the UA 100 according to a treatment plan. In addition, the computer 132 can send UA position control signals that cause the UA position controller 144 to adjust the UA positioning system 110 to set the position, orientation, and/or rotation of the UA 100, such as according to a treatment plan. Further, the computer 132 can send fluid circulation control signals to the fluid circulation system 150 to set the temperature set point of the cooling fluid and/or to set the speed of the fluid circulation pump.

The computer 132 can also receive feedback data or other information from the system electronics 140 and/or the fluid circulation system 150. For example, the RF controller 142 can send the actual RF power of the driving signals to the computer 132, and the computer 132 can make any adjustments on the RF power control signals as needed. Similarly, the UA position controller 144 can send the actual position, orientation, and/or rotation of the UA positioning system 110 to the computer 132, and the computer 132 can make any adjustments on the UA position control signals as needed. Further, the fluid circulation system 150 can send the actual temperature of the cooling fluid and/or the actual speed of the fluid circulation pump to the computer 132, and the computer 132 can make any adjustments on the fluid circulation control signals as needed. The computer 132 can also be in electrical communication with other devices or instruments that can independently monitor these components and provide independent feedback data. For example, an RF detector can monitor the driving signals generated by the RF controller 142 and provide feedback data to the RF controller 142 and/or to the computer 132. Similarly, a thermocouple can monitor the temperature of the cooling fluid and provide feedback data to the chiller and/or to the computer 132.

The computer 132 also receives ultrasound image data from the ultrasound imaging probe 120, which the computer 132 can use as feedback data to adjust the UA position control signals. The computer 132 can also use the ultrasound image data to align (e.g., automatically align) the distal tip of the UA 100 with the prostate and to register (e.g., automatically register) one or more reference locations on the UA 100 with the ultrasound images. For example, the UA 100 can include one or more fiducial marks that is/are opaque to ultrasound and, thus, visible in the ultrasound images. In addition, the shaft of the UA 100 can include two or more fiducial marks disposed along a reference line that is parallel to the longitudinal axis of the shaft. The computer 132 can determine the reference line by detecting the relative positions of the fiducial marks, using the ultrasound images, and can infer other aspects of the UA 100 based on their relationship to the reference line. The memory of computer 132 can have information regarding the relationship between the fiducial marks and other portions of the UA 100, such as the distance between the fiducial marks and other portions of the UA 100.

Alternatively, the ultrasound imaging probe 120 and the UA 100 can be integrated together as a single unit. In this embodiment, the ultrasound imaging probe 120 can acquire images of the surrounding tissues and/or anatomical structures. Software running on the computer 132 can determine the relative position of the integrated UA/imaging probe with respect to the prostate based on these images, such as through image recognition, machine learning, and/or other techniques, to achieve image registration and prostate alignment.

Figure 2:
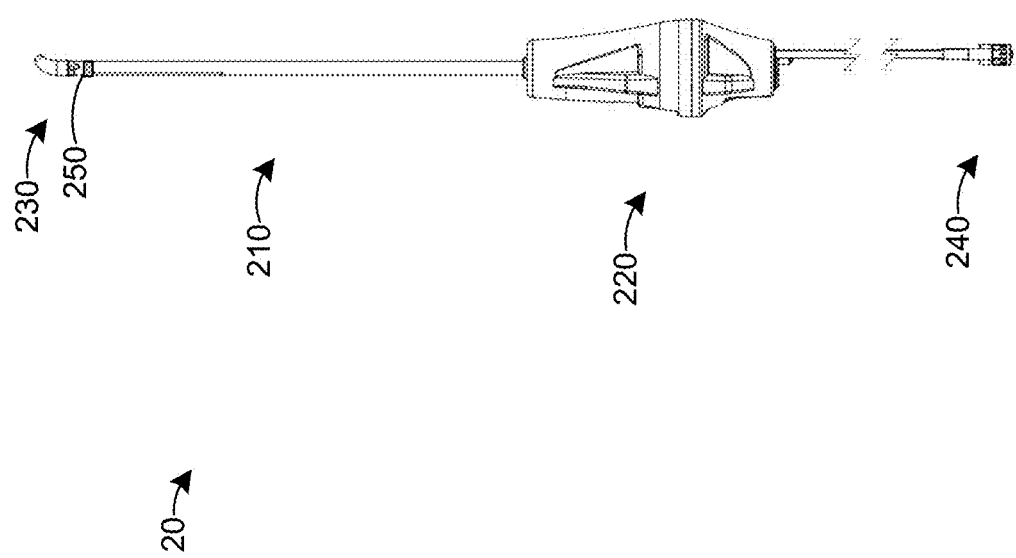
FIG. 2 is a side view of an example ultrasound applicator according to an embodiment.

FIG. 2 is a side view of an example ultrasound applicator 20 according to an embodiment. The ultrasound applicator 20 includes a shaft 210 that connects a handle 220 to a distal tip 230. One or more ultrasound transducers is/are disposed on the distal tip 230. A proximal end 240 of the ultrasound applicator 20 includes electrical connections that for receiving driving signals from an ultrasound controller, such as RF power controller 142. In addition, the proximal end includes inlet and outlet fluid couplings that can be fluidly coupled to a fluid circulation system (e.g., fluid circulation system 150) to circulation a cooling fluid within the ultrasound applicator 20. The ultrasound applicator 20 can be the same as or different than UA 100. In some embodiments, the ultrasound applicator 20 includes one or more ultrasound imaging elements 250 that acquire images of the surrounding tissues and/or anatomical structures to determine the relative location of the ultrasound applicator 20 with respect to the prostate.

Figure 3:
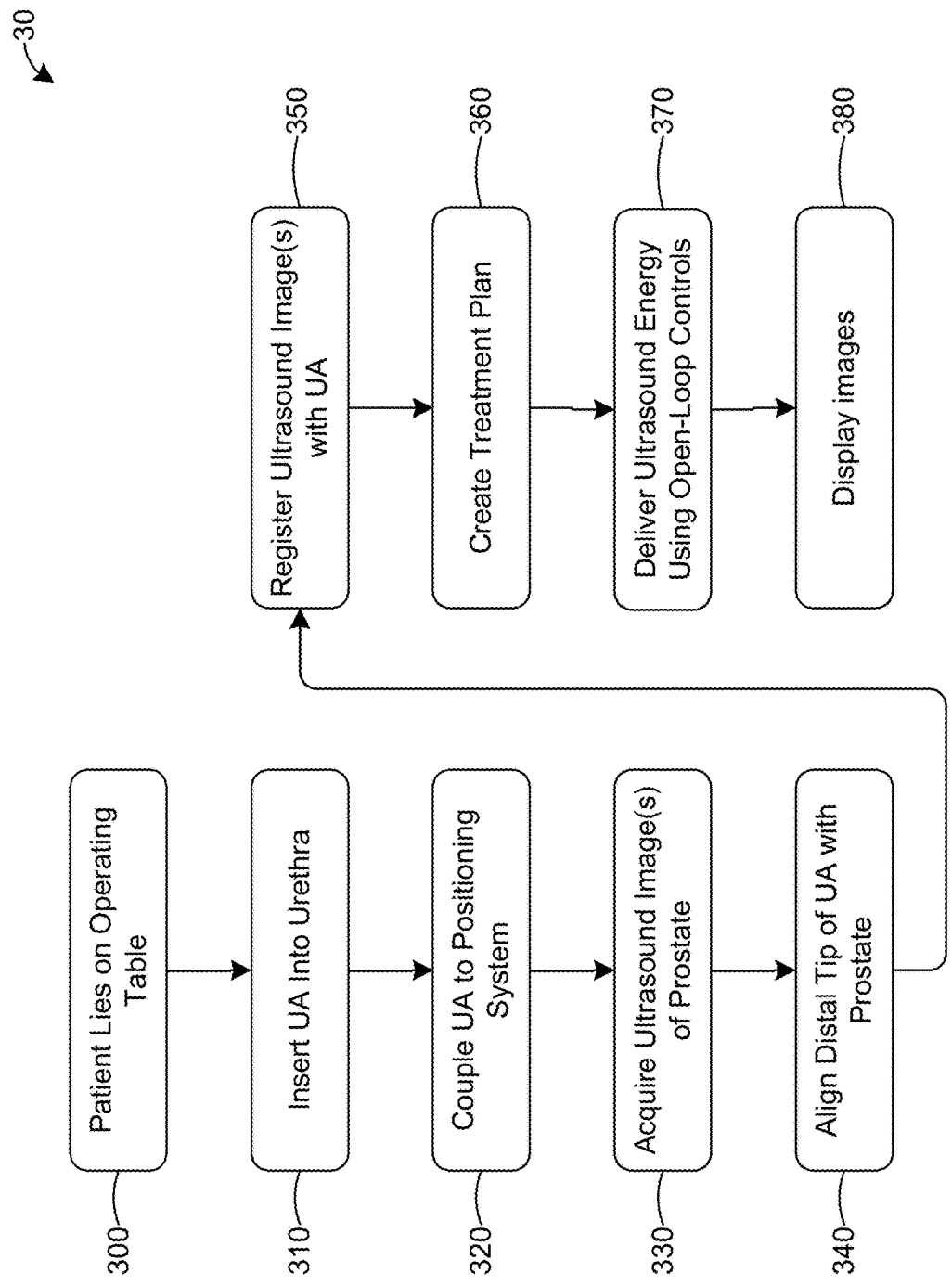
FIG. 3 is a flow chart of a method for open-loop ultrasound therapy according to one or more embodiments.

FIG. 3 is a flow chart 30 of a method for open-loop ultrasound therapy according to one or more embodiments. The system 10 can be used to perform one or more steps of flow chart 30. The method is performed using open-loop process controls without using temperature feedback data (e.g., MRI thermometry data).

In step 300, a patient lies (e.g., in a supine position) on an operating bed (e.g., patient support 170) or other working surface. The patient (e.g., patient 160) can be sedated before the procedure starts. In step 310, a medical clinician or technician inserts the distal tip of the UA 100 transurethrally into the patient's prostate. The distal tip of the UA 100 includes one or more ultrasound transducers that can generate therapeutic ultrasound energy. In step 220, the UA 100 is mechanically coupled to (e.g., mounted on) the UA positioning system 110. In some embodiments, step 320 can occur prior to step 310.

In step 330, the ultrasound imaging probe 120 is used to acquire ultrasound images of the prostate, urethra, and surrounding anatomy. The acquired ultrasound images can include multi-slice ultrasound images (e.g., a plurality of cross-sectional ultrasound images) or three-dimensional ultrasound images. Ultrasound image data representing the acquired ultrasound images are sent from the ultrasound imaging probe 120 to the computer 132. The computer 132 can optionally display the ultrasound images on the computer display 134. As discussed above, the ultrasound imaging probe 120 and the UA 100 can be integrated together as a single unit.

In step 340, the clinical operator remotely controls the UA 100 (e.g., by controlling the UA positioning system 110) to align the distal tip of the UA 100 with the prostate. The alignment can be based on the ultrasound images acquired and displayed in step 330 which can be used for visual feedback for the clinical operator. Alternatively, the computer 132 can use the ultrasound images to automatically align the distal tip of the UA 100 with the prostate by sending appropriate UA position control signals to the UA position controller 144. The computer 132 can use image recognition or machine learning to determine whether the distal tip of the UA 100 and the prostate are aligned and to generate UA position control signals to align the distal tip of the UA 100 and the prostate. Alternatively, when the imaging probe 120 is integrated into the UA 100, the computer 132 can use images acquired by the imaging probe 120 to determine how far to move the UA 100 to achieve registration to the prostate. Steps 330 and 340 can be performed simultaneously.

In step 350, the computer 132 registers the image(s) of the prostate with one or more reference locations (e.g., frames of reference) on the UA 100, such as one or more fiducial marks. For example, a fiducial mark can be located at a predetermined distance from the distal tip of the UA 100. The computer 132 can automatically locate the fiducial marks or the fiducial marks can be manually identified using the computer 132. Alternatively, the computer 132 can register the images with respect to the UA 100 which includes the imaging probe 120.

Figure 4:
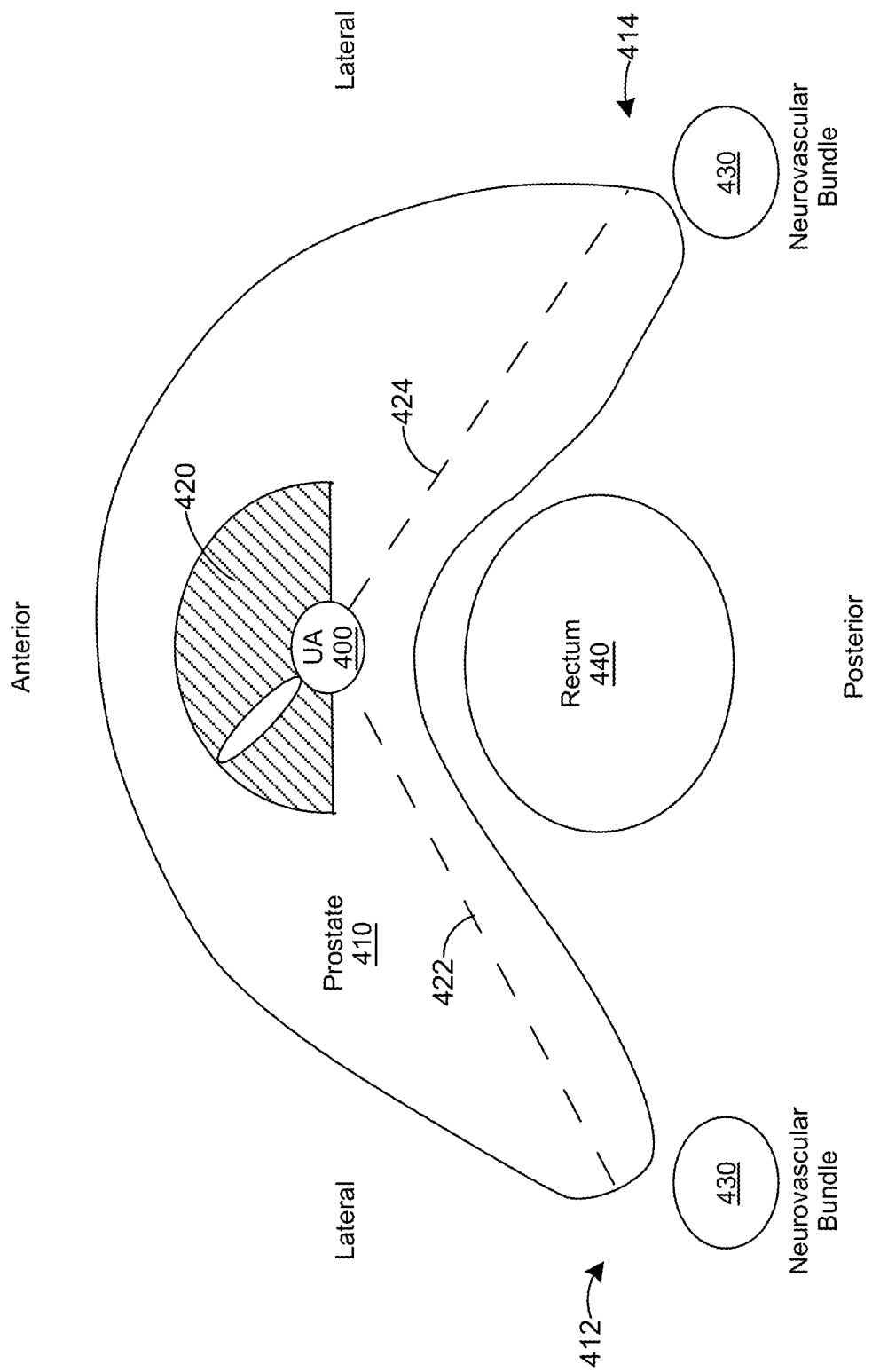
FIG. 4 is a cross-sectional view of an example ultrasound applicator in a prostate according to an embodiment.

Using the registered image(s), the clinical operator defines a treatment plan for the ultrasound therapy using the computer 132 at step 360. The treatment plan can include the radial, axial, and angular-range coordinates of the ultrasound therapy (e.g., ablation), which defines a target volume. The radial and/or the angular-range coordinates can vary as a function of the axial position. In some embodiments, the angular range can include an angular range of 0° up to about 280° including up to about 240°, which can correspond to the prostate's transition region (e.g., as illustrated in FIG. 4). The axial position can cover the region extending from the base of the prostate to some point close to the apex of the prostate. The radial coordinates are preferably configured to avoid the region beyond the prostate capsule. In general, the coordinates of the target volume are selected to avoid anatomically-sensitive areas such as the patient's neurovascular bundles, rectum, and internal organs other than the prostate. For example, the angular range coordinates can correspond to the anterior direction in the patient and/or the anterior and lateral directions in the patient, to avoid the patient's neurovascular bundles, rectum, and internal organs other than the prostate.

FIG. 4 is a cross-sectional view of an example ultrasound applicator 400 in a prostate 410 according to an embodiment. The treatment plan defines the treatment volume 420 such that the angular-range coordinates avoid the patient's neurovascular bundles 430 and rectum 440, which are generally in a posterior direction with respect to the ultrasound applicator 400. For example, the angular-range coordinates can include 0° (e.g., the left lateral side in FIG. 4) up to 180° (the right lateral side in FIG. 4). Alternatively, the angular-range coordinates can include 0° up to 240° where a 0° radial line 422 intersects the left transition region 412 and a 240° radial line 424 intersects the right transition region 414. In general, the angular-range coordinates correspond to lateral and/or anterior directions in the patient with respect to the ultrasound applicator 400. The angular-range coordinates can also avoid internal organs other than the prostate. Ultrasound applicator 400 can be the same as or different than ultrasound applicator 20 and UA 100.

Returning to FIG. 3, in step 370, the UA 100 delivers ultrasound energy according to the treatment plan using open-loop controls that do not include temperature-feedback data. The ablation occurs in the general anterior and/or lateral directions, with respect to UA 100, away from anatomically-sensitive areas such as the patient's neurovascular bundles and rectum (e.g., as illustrated in FIG. 4) and internal organs other than the prostate, which can increase the safety of the procedure. The ultrasound energy is delivered in an open-loop fashion (e.g., without temperature feedback such as MRI thermometry feedback), with the power levels and the rotation rate of the UA 100 controlled by software running in the computer 132. The UA 100 can be rotated by the UA positioning system 110. In an alternative embodiment, the UA 100 can include a plurality of transducers disposed about at least a portion of the circumference of the distal end of the UA 100. The transducers can be operated to direct ultrasound energy simultaneously in multiple angular directions, which can reduce treatment time as opposed to rotating the UA 100 over the full angular range of the target volume.

In step 380, the computer 132 optionally displays the ultrasound images on display 134. The ultrasound images (e.g., sagittal planar images) can be displayed using ultrasound image data collected by the ultrasound imaging probe 120. The computer 132 can also display a progress indicator showing the completion percentage of the procedure. In some embodiments, the computer 132 can overlay the treatment volume on the ultrasound images. Additional or other images can also be displayed. Step 380 can occur simultaneously with any of steps 330, 340, 350, 360, and/or 370.

In an aspect, the present system and method allows for cost-effective and clinically-adequate treatment of some conditions such as prostate enlargement using ultrasound energy directed by one or more ultrasound transducers in a suitable probe where the procedure is controlled in an open-loop fashion and without the need for MRI imaging. In some embodiments, the ultrasound transducers can comprise an ultrasound transducer array, which can be controlled (e.g., phase-controlled) to focus ultrasound and/or electronically steer the ultrasound. In one or more examples, a multi-slice image may be employed to inform a method, system or clinical operator on details of delivering a treatment. The treatment can include a plan involving a radial and/or axial spatial range for treatment.

Specifically, and in some aspects, an ultrasound therapy applicator can be inserted into the male urethra in combination with a trans-rectal ultrasound imaging probe for therapy applicator positioning and monitoring. In yet other aspects, the invention provides for continuous or substantially continuous treatment in combination with an open-loop treatment algorithm and treatment plan including appropriate treatment parameters, which in turn can include a rate of rotation of a therapy applicator about an axis thereof, a power level of one or more ultrasonic energy sources, and so on.

Auxiliary features of the invention can also include controlled cooling water circulation in a therapy device or location so as to control or reduce unwanted heat from accumulating therein. Sterile fluids such as water can be circulated in said device or location through a tube set using a peristaltic pump or other fluid driver. Cooling of a transurethral applicator and/or cooling of tissue using a rectal cooling device are possible implementations in some embodiments.

Another advantage of the systems and methods disclosed herein is the reduced cost of the procedure. This is the result of the reduced treatment time and the ability to conduct the procedure without using an MRI system.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in field-programmable gate arrays (FPGAs) or other semiconductor devices, or other tangible computer storage medium) encoded with one or more programs that, when executed on one or more computers or other processors, perform methods that implement one or more of the various embodiments described above. When implemented in software (e.g., as an application or "app"), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a personal digital assistant (PDA), a smartphone, or any other suitable portable or fixed electronic device.

Also, a computer may have one or more communication devices, which may be used to interconnect the computer to one or more other devices and/or systems, such as, for example, one or more networks in any suitable form. The networks can include a local area network, a wide area network, an enterprise network, an intelligent network (IN), a cellular network, a WiFi network, a virtual private network, or the Internet. Such networks may be based on any suitable technology and may operate according to any suitable protocol and may include wireless networks and/or wired networks.

Also, a computer may have one or more input devices and/or one or more output devices. These devices can be used, among other things, to present and/or manipulate a user interface. Examples of output devices that may be used to provide a user interface include printers or display screens for visual presentation of output and speakers or other sound generating devices for audible presentation of output. Examples of input devices that may be used to manipulate or interact with a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor, but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the present disclosure and claims include new and novel improvements to existing methods and technologies, which were not previously known nor implemented to achieve the useful results described above. Users of the present method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way unless stated otherwise. Accordingly, embodiments may be constructed in which acts are performed in an order different than illustrated, which may include performing some acts simultaneously, even though shown as sequential acts in illustrative embodiments.

What is claimed is:

1. A method for delivering ultrasound therapy using open-loop controls, comprising:
    inserting a distal tip of a therapeutic ultrasound applicator into a patient's urethra, the distal tip including an ultrasound transducer;
    acquiring ultrasound images of the patient's urethra and prostate with an ultrasound imaging probe;
    aligning the distal tip of the therapeutic ultrasound applicator with the patient's prostate using the ultrasound images;
    delivering therapeutic ultrasound energy to the patient's prostate, with the ultrasound transducer, according to a treatment plan, the treatment plan including a predetermined limited angular range for the therapeutic ultrasound energy, the predetermined limited angular range restricting the therapeutic ultrasound energy to only a lateral and/or an anterior direction between a left transition region of the prostate and a right transition region of the prostate to avoid delivering the therapeutic ultrasound energy in an angular direction of the patient's rectum, neurovascular bundles, and internal organs other than the patient's prostate;
    registering the ultrasound images with a reference location on the therapeutic ultrasound applicator to provide registered ultrasound images;
    in a computer, defining the treatment plan using the registered ultrasound images;
    wherein defining the treatment plan includes setting a predetermined limited radial range for the therapeutic ultrasound energy that avoids a region immediately beyond the patient's prostate and a predetermined limited axial range for the therapeutic ultrasound energy between a base and an apex of the patient's prostate;
    wherein the therapeutic ultrasound is delivered without temperature feedback data.

2. The method of claim 1, wherein the reference location comprises a fiducial mark.

3. The method of claim 1, wherein the predetermined limited angular range is 0° to 280°.

4. The method of claim 3, wherein:
    the predetermined limited angular range is 0° to 240°,
    0° corresponds to the prostate's left transition region, and
    240° corresponds to the prostate's right transition region.

5. The method of claim 1, further comprising mechanically coupling the therapeutic ultrasound applicator to an ultrasound applicator positioning system.

6. The method of claim 5, further comprising automatically aligning the distal tip of the therapeutic ultrasound applicator with the patient's prostate using the ultrasound applicator positioning system.

7. The method of claim 5, further comprising rotating the therapeutic ultrasound applicator, with the ultrasound applicator positioning system, over the predetermined limited angular range while the therapeutic ultrasound energy is delivered.

8. The method of claim 1, further comprising displaying the ultrasound images on a display that is in electrical communication with the ultrasound imaging probe.

9. The method of claim 1,
    wherein the distal tip of the therapeutic ultrasound applicator includes a plurality of ultrasound transducers that are disposed about at least a portion of a circumference of the distal tip, and
    the method further comprises simultaneously delivering therapeutic ultrasound energy to the patient's prostate, with the ultrasound transducers, in multiple angular directions.

10. The method of claim 9, further comprising rotating the therapeutic ultrasound applicator so that the ultrasound transducers, in combination, are swept across the predetermined limited angular range while simultaneously delivering therapeutic ultrasound energy to the patient's prostate in multiple angular directions.

11. The method of claim 1, wherein the therapeutic ultrasound is delivered without MRI thermometry feedback data.

12. The method of claim 1, wherein the ultrasound imaging probe is integrated into the therapeutic ultrasound applicator.

* * * * *